United States Patent [19]
Yasumoto et al.

[11] Patent Number: 5,089,612
[45] Date of Patent: Feb. 18, 1992

[54] THIADIAZINE COMPOUND AND METHOD FOR PREPARING SAME

[75] Inventors: Masahiko Yasumoto, Toride; Tohru Tsuchiya; Isao Shibuya, both of Tsukuba; Midori Goto, Abiko, all of Japan

[73] Assignee: Director General of Agency of Industrial Science and Technology, Tokyo, Japan

[21] Appl. No.: 486,401

[22] Filed: Feb. 28, 1990

[30] Foreign Application Priority Data

Mar. 8, 1989 [JP] Japan .................................. 1-55880

[51] Int. Cl.$^5$ .................. C07D 285/34; C07D 417/04; C07D 417/14; C07D 417/12
[52] U.S. Cl. ........................................ 544/8; 540/481; 540/598
[58] Field of Search ..................... 544/8; 540/481, 598

[56] References Cited

FOREIGN PATENT DOCUMENTS 56-57779  5/1981  Japan ..................................... 544/8

OTHER PUBLICATIONS

Abstract JP-A-56 57780 (Kokyo Fijutsuin) 5/20/1981.

*Primary Examiner*—John M. Ford
*Attorney, Agent, or Firm*—Birch, Stewart, Kolasch & Birch

[57] ABSTRACT

There is disclosed a novel thiadiazine, 2,6-bis(disubstituted amino)-4-dialkylthiocarbamoylimino-1,3,5-thiadiazine, and method for preparing same. According to the disclosure a compound useful for a medicine and agricultural chemical can be obtained efficiently by a one-step reaction using inexpensive raw materials.

9 Claims, No Drawings

THIADIAZINE COMPOUND AND METHOD FOR PREPARING SAME

FIELD OF THE INVENTION

The present invention relates to 2,6-bis(disubstituted amino)-4-dialkylthiocarbamoylimino-1,3,5-thiadiazines, which are novel thiadiazines, and a method for preparing them.

BACKGROUND OF THE INVENTION

It is known conventionally that many thiadiazine derivatives have physiological activities, and, for example, it is reported that some thiadiazine derivatives have excellent pharmacological effects on inflammatory maladies and cardiopathies. There are also 1,3,5-thiadiazine derivatives such as buprofegin that has a substituted amino group at 2-position of thiadiazine ring, developed as new type of vermin controller by Nihon Nohyaku, Japan, and recent development of thiadiazine derivatives for use in medicines and agricultural chemicals has been remarkable. However, the history of the synthesis of thiadiazine is short, and examples of the synthesis are few, many of which involve complex steps and use expensive raw materials.

BRIEF SUMMARY OF THE INVENTION

Therefore, an object of the present invention is to provide novel 1,3,5-thiadiazine compounds that will serve as intermediates of medicines and agricultural chemicals.

Another object of the present invention is to provide a method for preparing novel 1,3,5-thiadiazine compounds efficiently by a one-step reaction using inexpensive raw materials.

Other and further objects, features, and advantages of the invention will appear more fully from the following description.

DETAILED DESCRIPTION OF THE INVENTION

The inventors have conducted extensive research and found 1,3,5-thiadiazine compounds and a method for preparing them that meet the objects of the present invention, leading to completion of the invention.

That is, the present invention provides (1) a 2,6-bis(-disubstituted amino)-4-dialkylthio-carbamoylimino-1,3,5-thiadiazine compound represented by the following formula (I):

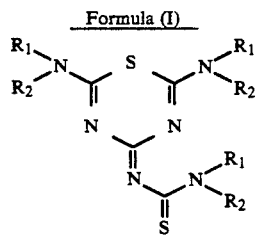

Formula (I)

wherein $R_1$ and $R_2$, which may be the same or different, each represent an alkyl group, or $R_1$ and $R_2$ may bond together to form a ring, and (2) a method for preparing a 2,6-bis(disubstituted amino)-4-dialkylthiocarbamoylimino-1,3,5-thiadiazine compound represented by formula (I) shown below, which is characterized in that an N,N-disubstituted cyanamide represented by formula (II) shown below is reacted with carbon disulfide under high pressure:

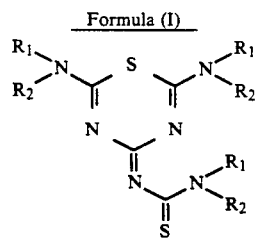

Formula (I)

wherein $R_1$ and $R_2$, which may be the same or different, each represent an alkyl group, or $R_1$ and $R_2$ may bond together to form a ring,

Formula (II)

wherein $R_1$ and $R_2$, each have the same meaning as in Formula (I).

N,N-disubstituted cyanamides represented by formula (II) that are used as raw material in the present invention can be readily obtained, and desired substituents can be introduced by selecting the types of $R_1$ and $R_2$. Alkyl group represented by $R_1$ and $R_2$ is an alkyl group having preferably 1 to 8 carbon atoms, more preferably 1 to 4 carbon atoms, most preferably 1 to 3 carbon atoms. Alkyl groups represented by $R_1$ and $R_2$ include, for example, a methyl group, an ethyl group, a propyl group, a tetramethylene group, and a pentamethylene group. When $R_1$ and $R_2$ bond together to form a ring, the ring is preferably a 3- to 8-membered ring, more preferably a 5- to 6-membered ring.

Although carbon disulfide, which is another raw material used in the present invention, can act as a reaction medium, if the raw material, i.e., an N,N-disubstituted cyanamide, is not dissolved in carbon disulfide, some other suitable solvent, such as methylene chloride or acetonitrile, can be used.

Although the molar ratio of the N,N-disubstituted cyanamide and carbon disulfide to be used is 3:1 stoichiometrically, the molar ratio is selected preferably in the range of 1:10 to 10:1, more preferably 1:5 to 5:1, most preferably 1:2 to 4:1.

The reaction of the present invention is carried out under pressure, and although a higher pressure is preferably used, the pressure to be used is selected preferably in the range of 1,000 to 9,000 atm, more preferably 3,000 to 8,000 atm, most preferably 5,000 to 8,000 atm. Although the reaction temperature is not particularly restricted, a temperature of 20° to 160° C. is desirably used, because undesirable side reactions, such as thermal decomposition, can be obviated. Reaction time in the present invention can be determined depending on the other conditions of reaction to be carried out, and usually it is preferably in the range of 2 to 50 hours, more preferably 2 to 30 hours, and most preferably 5 to 20 hours.

The 1,3,5-thiadiazine compounds obtained by the method of the present invention are novel compounds, and their use as medicines and agricultural chemicals and intermediates therefor can be expected. For example, as the results of pharmalogical test, anti-dementia and cancer-inhibiting effects of the compound according to the present invention have been discovered. The compound of the present invention has two substituted amino groups at 2- and 6-positions and, in particular, a thiocarbamoyl group at 4-position of thiadiazine ring. Since the thiocarbamoyl group has specific bonding force to metal ions, it is presumed that the compound would exhibit pharmacological effects by its selective bonding to an enzyme having metal of living body. Consequently the present invention is high in value of industrial application.

The present invention will now be described in more detail with reference to Examples, wherein parts are by weight, and percentages related to the yield are the theoretical percentages based on the raw material, i.e., N,N-disubstituted cyanamides.

EXAMPLE 1

4.7 parts of N,N-dimethylcyanamide and 25.3 parts of carbon disulfide were sealed in a Teflon (trade name) capsule, the capsule was placed in a high-pressure reaction tube, the pressure was elevated to about 4,000 atm, then the reaction tube was heated to a temperature of 100° C. Thereafter pressure was further applied to reach 5,000 atm, and the pressure was kept for 20 hours. Then after the temperature of the reaction tube was brought to room temperature and the pressure in the reaction tube was brought to normal pressure, the capsule was opened. The contents were washed out with ethyl ether, the crystalline product insoluble in the ether was filtered, and was recrystallized from ethanol, thereby obtaining 5.4 parts (yield:84 %) of the desired 2,6-bis(-dimethylamino)-4-dimethylthiocarbamoylimino-1,3,5-thiadiazine.

| $C_{10}H_{18}N_6S_2$ (molecular weight: 286.4; melting point: 257° C.) | | | |
|---|---|---|---|
| | C (%) | H (%) | N (%) |
| Calculated | 41.93 | 6.34 | 29.34 |
| Found | 41.78 | 6.28 | 29.32 |

EXAMPLE 2

After 11.2 parts of 1-piperidinecarbonitrile and 22.8 parts of carbon disulfide were kept under 8,000 atm at 70° C. for 20 hours using the same procedure as in Example 1, 7.6 parts (yield: 55 %) of the desired 2,6-bis(1-piperidyl)-4-pentamethylenethiocarbamoylimino-1,3,5-thiadiazine were separated in the same manner as in Example 1.

| $C_{19}H_{30}N_6S_2$ (molecular weight: 406.5; melting point: 210° C.) | | | |
|---|---|---|---|
| | C (%) | H (%) | N (%) |
| Calculated | 56.14 | 7.44 | 20.67 |
| Found | 56.02 | 7.47 | 20.63 |

EXAMPLE 3

After 10.1 parts of 1-pyrrolidinecarbonitrile and 40.3 parts of carbon disulfide were kept under 8,000 atm at 50° C. for 20 hours using the same procedure as in Example 1, 9.1 parts (yield: 71%) of the desired 2,6-(1-pyrolidyl)- 4-tetramethylenethiocarbamoylimino-1,3,5-thiadiazine were separated in the same manner as in Example 1.

| $C_{16}H_{24}N_6S_2$ (molecular weight: 364.5; melting point: 181° C) | | | |
|---|---|---|---|
| | C (%) | H (%) | N (%) |
| Calculated | 52.72 | 6.64 | 23.05 |
| Found | 52.55 | 6.69 | 23.00 |

What we claim is:

1. A 2,6-bis(disubstituted amino)-4-dialkyl-thiocarbamoylimino-1,3,5-thiadiazine compound represented by the following formula (I):

Formula (I)

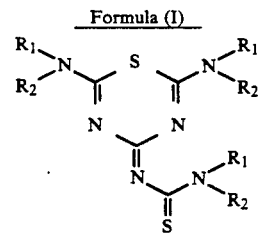

wherein $R_1$ and $R_2$, which may be the same or different, each represent a $C_{1-8}$ alkyl group, or $R_1$ and $R_2$ may bond together to form a 3- to 8-membered ring.

2. The 1,3,5-thiadiazine compound as claimed in claim 1, wherein the alkyl group represented by $R_1$ or $R_2$ is selected from the group consisting of methyl, ethyl, propyl, tetramethylene, and pentamethylene.

3. The 1,3,5-thiadiazine compound as claimed in claim 1, wherein $R_1$ and $R_2$ bond together to form a 3- to 8-membered ring.

4. A method for preparing a 2,6-bis-(disubstituted amino)-4-dialkylthiocarbamoylimino-1,3,5-thiadiazine compound represented by formula (I) shown below, which comprises reacting an N,N-disubstituted cyanamide represented by formula (II) shown below with carbon disulfide under high pressure:

Formula (I)

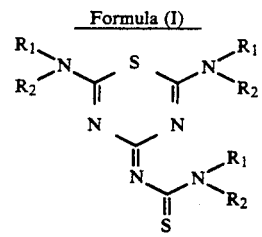

wherein $R_1$ and $R_2$, which may be the same or different, each represent a $C_{1-8}$ alkyl group, or $R_1$ an $R_2$ may bond together to form a 3- to 8-membered ring,

Formula (II)

wherein $R_1$ and $R_2$ each have the same meaning as in Formula (I).

5. The method as claimed in claim 4, wherein the alkyl group represented by $R_1$ or $R_2$ is selected from the group consisting of methyl, ethyl, propyl, tetramethylene and pentamethylene.

6. The method as claimed in claim 4, wherein $R_1$ and $R_2$ bond together to form a 3- to 8-membered ring.

7. The method as claimed in claim 4, wherein the molar ratio of the N,N-disubstituted cyanamide and carbon disulfide is selected in the range of 1:10 to 10:1.

8. The method as claimed in claim 4, wherein the pressure is selected in the range of 1,000 to 9,000 atm.

9. The method as claimed in claim 4, wherein the reaction temperature is selected in the range of 20° C. to 160° C.

* * * * *